(12) United States Patent
Eidenschink et al.

(10) Patent No.: US 9,339,260 B2
(45) Date of Patent: May 17, 2016

(54) APPARATUS AND METHOD FOR SEALING A VESSEL PUNCTURE OPENING

(75) Inventors: Tracee Eidenschink, Wayzata, MN (US); Jan Weber, Maastricht (NL); Lilliana Atanasoska, Edina, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 89 days.

(21) Appl. No.: 13/370,793

(22) Filed: Feb. 10, 2012

(65) Prior Publication Data

US 2012/0172928 A1 Jul. 5, 2012

Related U.S. Application Data

(63) Continuation of application No. 11/948,554, filed on Nov. 30, 2007, now abandoned.

(51) Int. Cl.
| | |
|---|---|
| *A61B 17/00* | (2006.01) |
| *A61B 17/12* | (2006.01) |
| *A61F 2/07* | (2013.01) |
| *A61F 2/91* | (2013.01) |

(52) U.S. Cl.
CPC ......... *A61B 17/0057* (2013.01); *A61B 17/1219* (2013.01); *A61B 17/12022* (2013.01); *A61B 17/12159* (2013.01); *A61B 17/12172* (2013.01); *A61B 17/12177* (2013.01); *A61B 2017/00867* (2013.01); *A61B 2017/00871* (2013.01); *A61F 2/07* (2013.01); *A61F 2/91* (2013.01); *A61F 2250/0023* (2013.01)

(58) Field of Classification Search
CPC ..................... A61B 17/0057; A61B 17/12022; A61B 17/12159; A61B 17/12172; A61B 17/12004; A61B 17/12118; A61B 2017/00575; A61B 2017/00592; A61B 2017/0061; A61B 2017/00615; A61B 2017/00628; A61B 2017/12095; A61B 2017/12054; A61B 2017/00637; A61B 2017/00672; A61B 2017/00676; A61B 2017/00659
USPC ........................... 606/151, 213; 623/1.1–1.54
See application file for complete search history.

(56) References Cited

U.S. PATENT DOCUMENTS

| | | |
|---|---|---|
| 4,852,568 A | 8/1989 | Kensey |
| 4,890,612 A | 1/1990 | Kensey |
| 5,021,059 A | 6/1991 | Kensey et al. |
| 5,061,274 A | 10/1991 | Kensey |
| 5,350,399 A | 9/1994 | Erlebacher et al. |

(Continued)

FOREIGN PATENT DOCUMENTS

| | | |
|---|---|---|
| EP | 0534696 A1 | 3/1993 |
| WO | 2006034114 A2 | 3/2006 |

*Primary Examiner* — Alexander Orkin
(74) *Attorney, Agent, or Firm* — Seager, Tufte & Wickhem LLP

(57) ABSTRACT

A device for sealing a puncture opening may include a base frame having a delivery configuration, wherein the base frame is retracted to have a relatively smaller overall profile, and a deployed configuration, wherein the base frame is extended to have a relatively larger overall profile. The base frame is sized to engage an interior surface of the blood vessel wall in the deployed configuration. A sealing section is coupled to the base frame, the sealing section having an initial configuration, wherein the sealing section permits fluid flow, and a barrier configuration, wherein the sealing section prevents fluid flow. The sealing section in the barrier configuration is sized to block fluid flow through the puncture opening when the base frame is in the deployed configuration.

1 Claim, 6 Drawing Sheets

(56) References Cited

U.S. PATENT DOCUMENTS

| | | | |
|---|---|---|---|
| 5,383,899 A | | 1/1995 | Hammerslag |
| 5,591,195 A | * | 1/1997 | Taheri et al. ................. 623/1.11 |
| 5,769,870 A | * | 6/1998 | Salahieh et al. ............. 606/198 |
| 5,855,565 A | | 1/1999 | Bar-Cohen et al. |
| 6,080,182 A | * | 6/2000 | Shaw et al. ................... 606/213 |
| 6,120,524 A | * | 9/2000 | Taheri ........................... 606/213 |
| 6,585,758 B1 | | 7/2003 | Chouinard et al. |
| 6,969,395 B2 | | 11/2005 | Eskuri |
| 6,997,948 B2 | | 2/2006 | Stinson |
| 7,029,494 B2 | | 4/2006 | Soun et al. |
| 7,834,527 B2 | * | 11/2010 | Alvarez Icaza Rivera et al. ............................. 310/344 |
| 2002/0165601 A1 | * | 11/2002 | Clerc ........................... 623/1.13 |
| 2002/0165606 A1 | * | 11/2002 | Wolf et al. ................... 623/1.24 |
| 2003/0130720 A1 | * | 7/2003 | DePalma et al. ............. 623/1.13 |
| 2005/0037050 A1 | | 2/2005 | Weber |
| 2005/0107867 A1 | | 5/2005 | Taheri |
| 2005/0149176 A1 | * | 7/2005 | Heggestuen et al. ........ 623/1.46 |
| 2005/0267570 A1 | | 12/2005 | Shadduck |
| 2006/0009835 A1 | * | 1/2006 | Osborne et al. ............. 623/1.13 |
| 2007/0078492 A1 | * | 4/2007 | Tozzi et al. .................... 607/35 |
| 2007/0112383 A1 | * | 5/2007 | Conlon et al. ................ 606/232 |
| 2007/0167980 A1 | * | 7/2007 | Figulla et al. ................ 606/213 |
| 2007/0276470 A1 | | 11/2007 | Tenne |
| 2008/0262596 A1 | * | 10/2008 | Xiao ............................ 623/1.14 |
| 2008/0269866 A1 | * | 10/2008 | Hamer et al. ................ 623/1.11 |
| 2009/0054965 A1 | * | 2/2009 | Richard ....................... 623/1.15 |

* cited by examiner

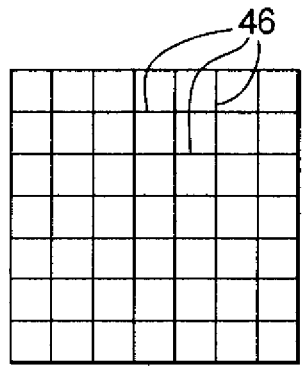
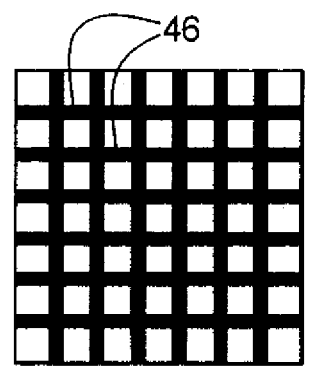
*FIG. 4A*  *FIG. 4B*
*FIG. 5*
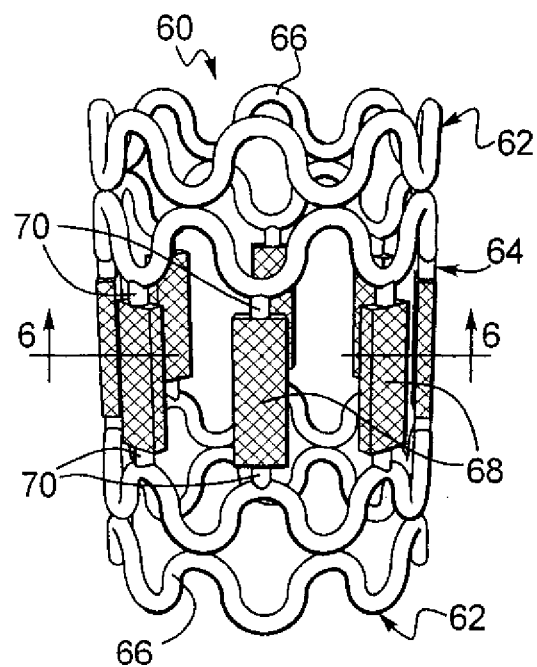
*FIG. 6*
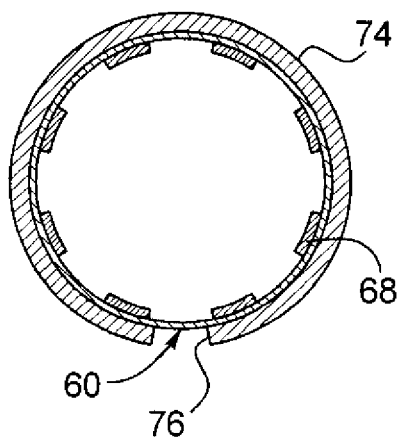

FIG. 7
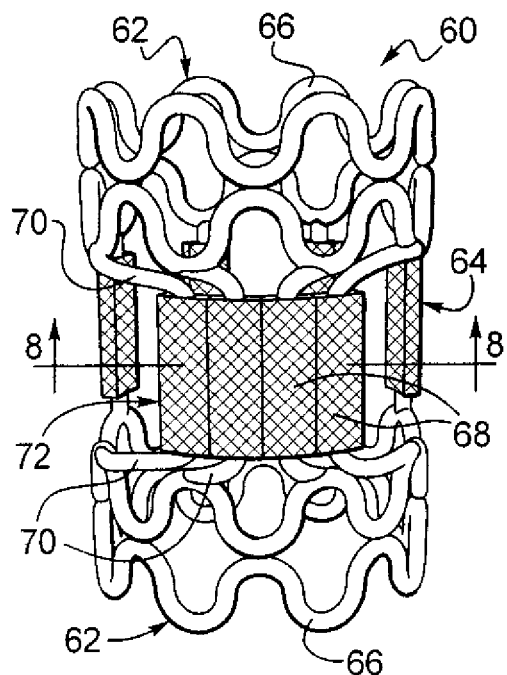
FIG. 8
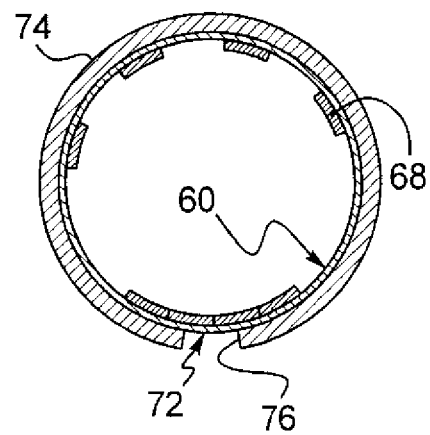
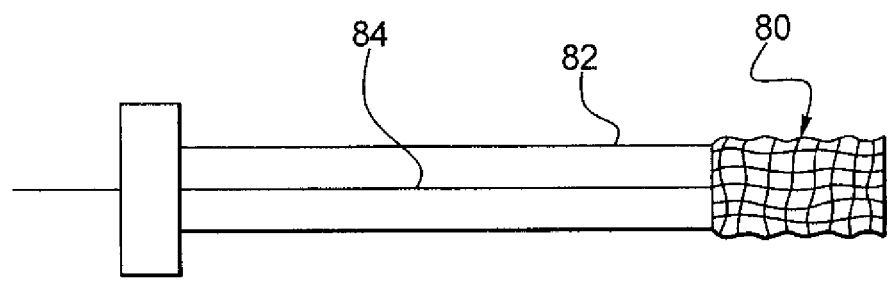
FIG. 9

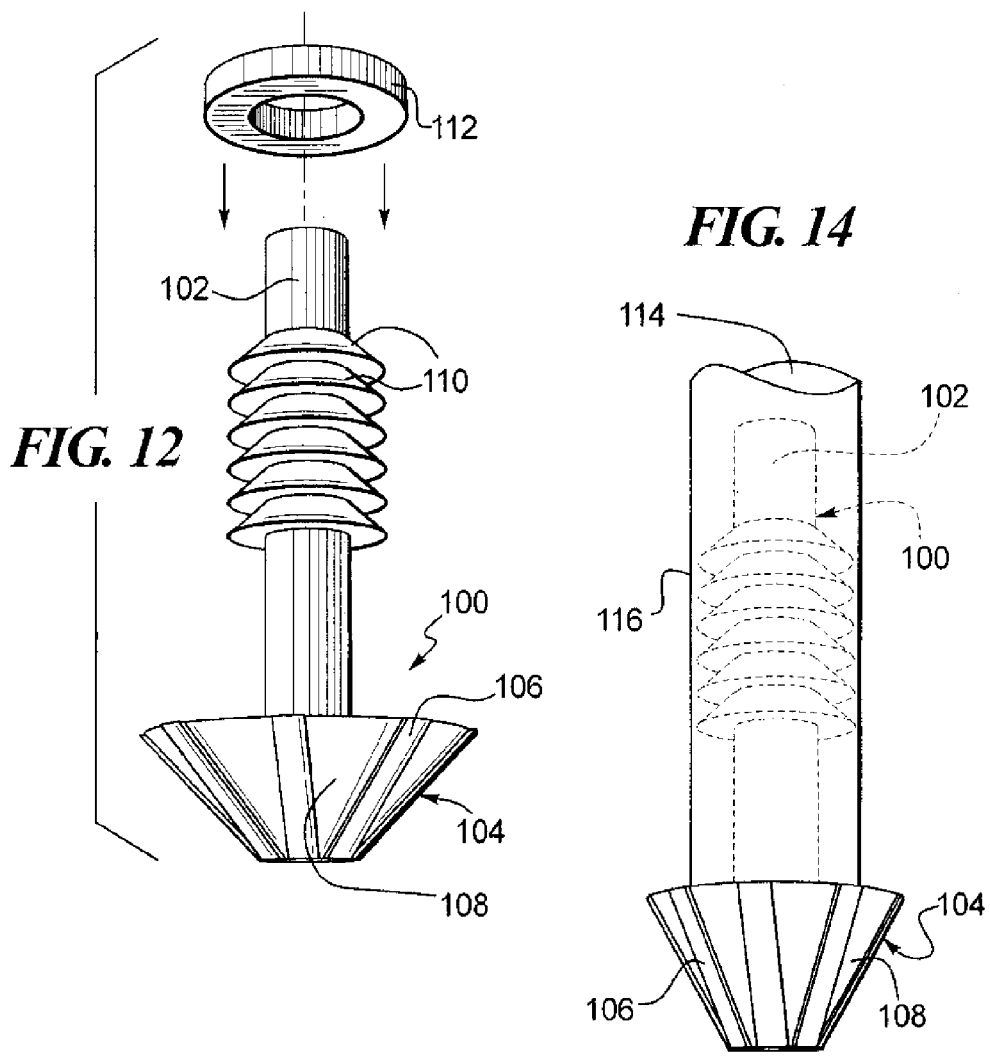
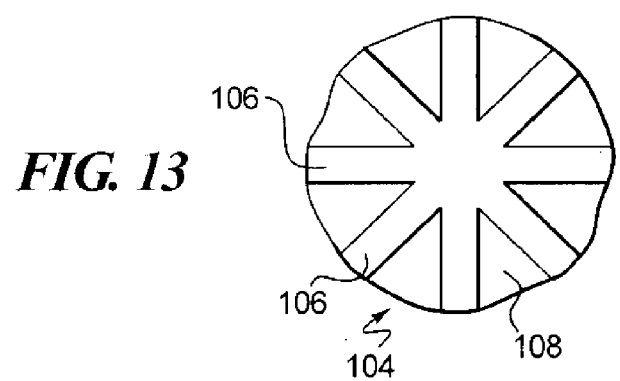

APPARATUS AND METHOD FOR SEALING A VESSEL PUNCTURE OPENING

RELATED APPLICATIONS

This application is a continuation of U.S. application Ser. No. 11/948,554 filed Nov. 30, 2007.

FIELD OF THE DISCLOSURE

The present disclosure generally relates to medical devices and methods, and more particularly to apparatus and methods for sealing a puncture opening after a surgical procedure.

BACKGROUND OF THE DISCLOSURE

A large number of diagnostic and interventional procedures involve the percutaneous introduction of instrumentation into a vein or artery. For example, coronary angioplasty, angiography, atherectomy, stenting of arteries, and many other procedures often involved accessing the vasculature through a catheter placed in the femoral artery or other blood vessel. Once the procedure is completed and the catheter or other instrumentation is removed, bleeding from the punctured artery must be controlled.

Traditionally, external pressure has been applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and maybe unsuitable amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274. Anther approach to subcutaneous blood vessel puncture closure involves the delivery of non-absorbable tissue adhesives, such as cyanoacrylate, to the perforation site. Such a system is disclosed in U.S. Pat. No. 5,383,899.

The use of these conventional devices presents several drawbacks, including: (1) Complex and difficult applications; (2) Partial occlusion of the blood vessel by the anchor when placed properly; and (3) Complete blockage of the blood vessel or a branch of the blood vessel by the anchor if placed improperly.

More recently, sealing methods have been disclosed which use an energy source, such as heat, to seal the puncture. These methods are a significant departure from the well-known pressure- or plug-based methods and can require a practitioner to learn an entirely new procedure using unfamiliar devices.

Accordingly, it would be desirable to provide apparatus that reliably seals vessel puncture openings using methods that are already familiar to the practitioner.

SUMMARY OF THE DISCLOSURE

A device for sealing a puncture opening in a wall of a blood vessel may include a base frame movable between a delivery configuration, in which the base frame is retracted to have a relatively smaller overall profile, and a deployed configuration, in which the base frame is extended to have a relatively larger overall profile. The base frame is sized to engage an interior surface of the blood vessel wall when in the deployed configuration, and is configured to have a first stable state corresponding to the deployed configuration. A sealing section may be coupled to the base frame and have an initial configuration which permits fluid flow through the sealing section and a barrier configuration which prevents fluid flow through the sealing section. The sealing section in the barrier configuration is sized to block fluid flow through the puncture opening when the base frame is in the deployed configuration.

In a refinement a device for sealing a puncture opening in a wall of a blood vessel may include a base frame movable between a delivery configuration, in which the base frame is retracted to have a relatively smaller overall profile, and a deployed configuration, in which the base frame is extended to have a relatively larger overall profile. The base frame is sized to engage an interior surface of the blood vessel wall when in the deployed configuration, and is configured to have a first stable state corresponding to the deployed configuration. A sealing section is coupled to the base frame and includes a bi-stable material having a first stable state corresponding to an initial configuration of the sealing section, in which the sealing section permits fluid flow, and a second stable state corresponding to a barrier configuration of the sealing section, in which the sealing section prevents fluid flow. The sealing section in the barrier configuration is sized to block fluid flow through the puncture opening when the base frame is in the deployed configuration.

In a further refinement, a device for sealing a puncture opening in a wall of a blood vessel may include a base frame including a first bi-stable material having a first stable state corresponding to a delivery configuration of the base frame, in which the base frame is retracted to have a relatively smaller overall profile, and a second stable state corresponding to a deployed configuration of the base frame, in which the base frame is extended to have a relatively larger overall profile. The base frame is sized to engage an interior surface of the blood vessel wall when in the deployed configuration. A sealing section is coupled to the base frame and includes a second bi-stable material having a first stable state corresponding to an initial configuration of the sealing section, in which the sealing section permits fluid flow, and a second stable state corresponding to a barrier configuration of the sealing section, in which the sealing section prevents fluid flow. The sealing section in the barrier configuration is sized to block fluid flow through the puncture opening when the base frame is in the deployed configuration.

BRIEF DESCRIPTION OF THE DRAWINGS

The foregoing aspects and many of the attendant advantages of this disclosure will become more readily appreciated as the same becomes better understood by reference to the following detailed description, when taken in conjunction with the accompanying drawings, wherein:

FIGS. 4A and 4B are schematic illustrations showing filaments of the puncture sealing stent in delivery and deployed configurations, respectively;

FIG. 5 is a perspective view of a further embodiment of a puncture sealing stent in a delivery configuration, made in accordance with the present disclosure;

FIG. 6 is a cross-sectional view of the puncture sealing stent taken along line 6-6 of FIG. 5;

FIG. 7 is a perspective view of the puncture sealing stent of FIG. 5 in the deployed configuration;

FIG. 8 is a cross-sectional view of the puncture sealing stent taken along 8-8 of FIG. 7;

FIG. 9 is a side elevation view of an alternative embodiment of a puncture sealing stent coupled to an introducer for delivery;

FIG. 12 is a perspective view of yet another embodiment of a blood vessel sealing device according to the present disclosure;

FIG. 13 is a top plan view of the sealing device of FIG. 12;

FIG. 14 is a side elevation view of the sealing device of FIG. 12 as inserted into an introducer.

It should be understood that the drawings are not necessarily to scale and that the embodiments are sometimes illustrated by phantom lines, diagrammatic representations, and fragmentary views. In certain instances, details may have been omitted which are not necessary for an understanding of the disclosed puncture sealing devices which would render other details difficult to perceive. It should be understood, of course, that this disclosure is not necessarily limited to the particular embodiments illustrated herein.

DETAILED DESCRIPTION

Various embodiments of a blood vessel puncture sealing device are disclosed herein having a base frame and a sealing section. The base frame is movable from a first, generally contracted configuration during delivery to a second, generally expanded configuration for engaging the vessel wall when deployed. The sealing section is coupled to the base frame and similarly has an initial configuration which permits fluid flow and a barrier configuration which prevents fluid flow through at least a portion of the sealing section. When in the barrier configuration, the sealing section forms a barrier that closes off the vessel puncture opening, thereby facilitating hemostasis.

The base frame is configured to have a stable state corresponding to the deployed configuration. This stable state may be the only stable state for the base frame, in which case the base frame must be held in the delivery configuration prior to deployment. The base frame may be held in the delivery configuration by mechanical means (such as by a delivery tube or clamp), electrical means (such as a current source acting on an electroactive polymer), or other restricting means. Alternatively, the base frame may also have a second stable state corresponding to the delivery configuration, in which case the base frame may be said to have a "bi-stable" structure.

The sealing section also includes at least one stable state corresponding to the barrier configuration of the sealing section. It may also have a second stable state corresponding to the initial configuration, in which case the sealing section also includes a bi-stable structure.

In some of the embodiments described herein, the sealing device is described as a stent, which has heretofore been primarily used to prop open vascular structures. As used herein, the term "stent" is intended to encompass any type of device that is sized for insertion into a vascular structure and which may be configured to engage a wall of the vascular structure while defining a central passage through which vessel fluid may flow. Furthermore, this disclosure is not limited to the use of stents to close vessel punctures but instead covers all structures falling within the scope of the claims.

Figure 1:
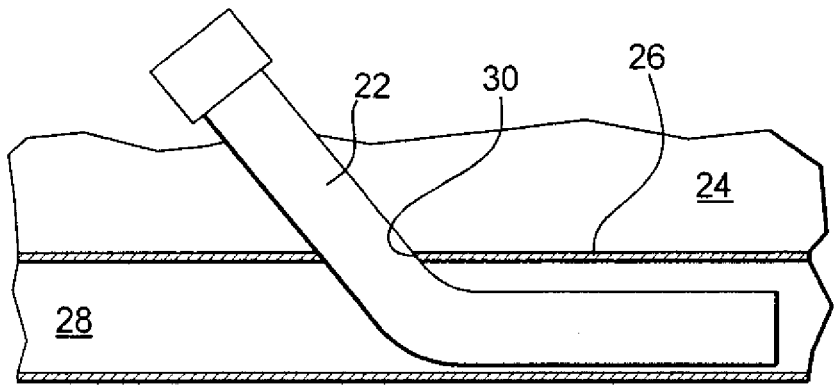
FIG. 1 is a side-elevation view, in cross-section, of an introducer inserted into a blood vessel during a medical procedure.
Figure 2:
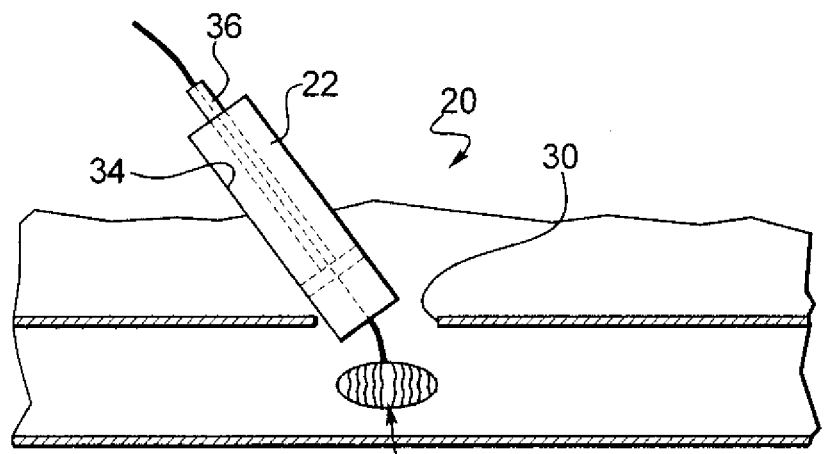
FIG. 2 is a side-elevation view, in cross-section, of the introducer of FIG. 1 being used to deliver a puncture sealing stent in a delivery configuration, made in accordance with this disclosure.
Figure 3:
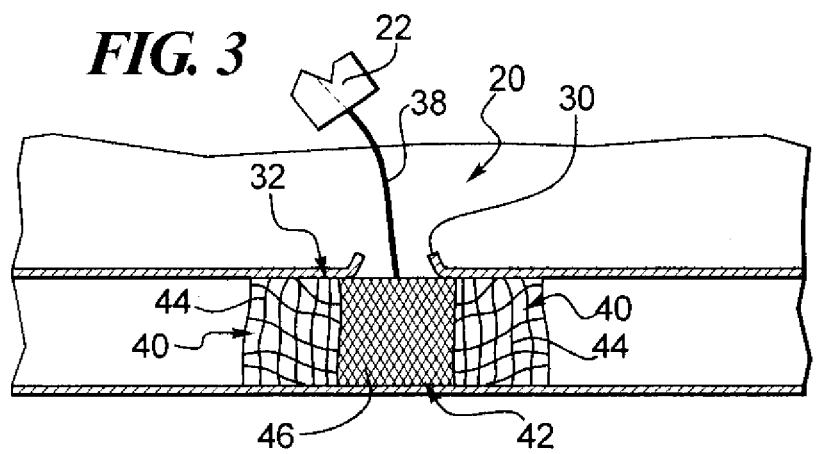
FIG. 3 is a side elevation view in cross-section, of the stent of FIG. 2 in a deployed configuration.

A first embodiment of a sealing device 20 in accordance with the disclosure is illustrated in FIGS. 1-3. The sealing device 20 may be used with an introducer 22, which may be inserted through bodily tissue 24 and through a wall 26 of a blood vessel 28 so that a distal end of the introducer 22 resides within the blood vessel 28, as shown in FIG. 1. The introducer 22 passes through a puncture opening 30 formed in the blood vessel wall 26. The introducer 22 will typically be in this position upon the conclusion of a medical procedure in which the blood vessel 28 is used as a pathway to guide the use of catheters or other devices. As illustrated in FIG. 1, all of the medical devices used during the procedure have removed and the introducer 22 remains in place for use during the sealing procedure described below.

In FIG. 2, the sealing device 20 is shown having a base frame in the form of a self-expanding, puncture sealing stent 32. The stent 32 may be delivered into the blood vessel 28 through the introducer 22. More specifically, the introducer 22 has been withdrawn in a proximal direction so that the distal end of the introducer 22 is outside of but adjacent the puncture opening. During delivery, the puncture sealing stent 32 is in a contracted, delivery configuration to have a profile sized for passage through a lumen 34 of the introducer 22. The stent 32 may be advanced through the introducer 22 by a slidable pusher 36. The stent 32 may include a tether 38 to assist in positioning the stent 32 with respect to the puncture opening. More specifically, the tether 38 may be pulled in the proximal direction so that the stent 32 engages an inner surface of the blood vessel 28 and is centered with respect to the puncture 30.

Once inside the blood vessel, the puncture sealing stent 32 is self-expanding to a deployed configuration as shown in FIG. 3. In the deployed configuration, the stent is sized to engage an interior of the vessel wall. In the embodiment shown in FIG. 3, the puncture sealing stent 32 includes first and second anchor sections 40 disposed on opposite ends of a central sealing section 42. The anchor sections form a base frame that is moveable between the delivery and deployed configurations. The anchor sections 40 may also be configured to engage the blood vessel wall when in the expanded configuration, thereby to securely position the stent 32 with respect to the puncture 30. In the illustrated embodiment, the anchor sections 40 include filaments 44 formed in a first stent architecture adapted to engage the blood vessel wall when the stent 32 is in the expanded configuration. As illustrated, the filaments 44 of the first stent architecture are loosely, or diffusely, spaced.

The stent 32 has a stable state when in the deployed configuration. Accordingly, the filaments 44 automatically assume the deployed configuration when the device 20 is disposed in the blood vessel 28. Assumption of the deployed configuration may be driven by the mechanical structure and layout of the filaments 44 themselves, as in the current embodiment, or may be effected by some other means as described in the additional embodiments below. The sealing device 20 may further have a second stable state corresponding to the delivery configuration, in which case it would be a bi-stable structure.

The sealing section 42 coupled to the stent 32 may move from an initial configuration to a barrier configuration, in which the sealing section forms a barrier structure adapted to cover the vessel puncture 28. While the embodiment illustrated in FIGS. 1-3 shows the barrier structure as filaments 46, it may be formed by other structures such as panels, polymeric film, or collagen. The filaments 46 may be formed with a second stent architecture that automatically assumes the barrier configuration when the stent 32 is deployed, or they may be selectively placed into the barrier configuration as described in greater detail below. In the embodiment illustrated in FIG. 3, the filaments 46 of the second stent architecture are tightly or densely spaced. Additionally or alternatively, the second stent architecture may be formed by a plurality of braided filaments.

To facilitate hemostasis, the filaments 46 of the sealing section 42 may be formed at least in part with an expandable material. The expandable material may be a shape memory polymer that automatically increases volume in response to heat, moisture, or other conditions that change once the puncture sealing stent 32 is disposed within the blood vessel, thereby to move the sealing section from the initial configuration to the barrier configuration. Alternatively, the expandable material may be an electroactive polymer ("EAP") that is responsive to electric current to cause a similar volume change. If the expandable material is provided as an EAP, the tether 38 may also form an electrode that is coupled to the sealing section 42 for delivering electric current from a source. The filaments 46 in the sealing section 42 may be formed entirely of the expandable material or may include a substrate on which the expandable material is deposited.

Electroactive polymers, members of a family of plastics referred to as "conducting polymers," are a class of polymers characterized by their ability to change volume, and therefore influence the overall shape of the material, in response to electrical stimulation. They typically structurally feature a conjugated backbone and have the ability to increase electrical conductivity under oxidation or reduction. Some common electroactive polymers are polyaniline, polysulfone, polypyrrole, and polyacetylene. These materials are semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionicly conductive electrolyte medium that is coupled to the polymer surface. The electrolyte may be, for example, a gel, a solid, or a liquid. If ions are already present in the polymer when it is oxidized or reduced, they may exit the polymer. Dimensional changes may be effected in certain conducting polymers by the mass transfer of ions into or out of the polymer. For example, in some conducting polymers, the expansion is due to ion insertion between chains, whereas in others interchange repulsion is the dominant effect. Thus, the mass transfer of ions both into and out of the material leads to an expansion or contraction of the polymer.

The shape memory and electroactive polymers described above are examples of "bi-stable" materials having at least first and second stable states. As used herein, a "stable state" is a particular volume size and configuration of a material that exists in a given set of environmental conditions and which does not require an outside mechanical force to retain the particular volume and configuration. Materials that have two or more stable states are referred to herein as "bi-stable materials." An example of a structure having a single stable state is a self-expanding stent, in which the stable state corresponds to the expanded configuration of the stent. Such a stent requires an enclosure or other mechanically restrictive structure to retain it in a contracted state. Examples of bi-stable materials are the above-described shape memory and electroactive polymers. These materials have a first stable state based on a first set of environmental conditions (such as heat, moisture, supplied current, etc.) and a second stable state based on a second set of environmental conditions. Outside mechanical means are not required to hold these materials in their respective stable state shapes.

The bi-stable structure may actuate a sealing device to the deployed configuration in a variety of manners. In the current embodiment, where the filaments 46 of the sealing section 42 are tightly spaced, the expandable material may swell to assume the barrier configuration. As schematically illustrated in FIGS. 4A and 4B, the sealing section filaments may have contracted and expanded profiles. The filaments may be in the contracted profile (i.e., an initial configuration) as the puncture sealing stent 32 is inserted into the blood vessel. Once the expandable material is actuated, such as by applying or removing electrical current in the case of an EAP material, the filaments may swell to the expanded profile (i.e., a barrier configuration), thereby to completely eliminate or reduce the size of the passages between adjacent filaments as shown in FIG. 4B. The filaments may be sized and positioned such that the sealing section substantially prevents any blood from flowing therethrough when in the barrier configuration. Accordingly, with the stent 32 positioned so that the sealing section overlies the puncture opening, blood flow through the puncture opening will be prevented.

An alternative sealing device is illustrated in FIGS. 5-8 as a stent 60 in which a bi-stable material repositions elements of the stent 60 rather than swells to form a barrier. Turning first to FIG. 5, the stent 60 is shown having anchor sections 62 on opposite ends of a sealing section 64. The anchor sections 62 include filaments 66 configured to expand once placed inside of the blood vessel, thereby to grip the wall of the vessel and secure the stent 60 in place. The sealing section 64 includes a plurality of slats 68. The slats 68 are elongate members having complementary shaped edge surfaces that allow the slats 68 to fit closely together when moved to a barrier configuration, thereby to form a composite barrier. In the illustrated embodiment, the slats have linear side edges, but it will be appreciated that the side edges may have any shape as long as the pairs of facing edges on adjacent slats 68 are complementary.

The sealing section 64 further includes movable joints 70 made of a bi-stable material for connecting the opposite ends of each slat 68 to respective anchor sections 62 of the stent. Each joint 70 is formed of an expandable material that moves in response to a change in one or more conditions. For example, the joints 70 may be formed of or include an EAP material having a contracted, initial configuration. Upon the application of electrical current, the joints 70 may move to an expanded, barrier configuration. The joints may be shaped and/or oriented so that movement from the initial configuration to the barrier configuration is in a selected direction, thereby to move the slats 68 in a desired manner.

Referring to the drawings, the contracted configuration is illustrated in FIG. 5, where the slats 68 are spaced from one another. In FIG. 7, the joints 70 have been expanded to move four of the slats 68 toward each other until they contact and form a composite barrier 72. It will be appreciated that, instead of expansion, the stent 60 may use contraction of the bi-stable element to move the slats 68 to the deployed configuration.

In use, the stent 60 may be inserted into a blood vessel 74 having a puncture opening 76. As the stent 60 is positioned inside the blood vessel 74, the sealing section 64 is in the initial configuration as shown in FIG. 6. Once suitably positioned within the blood vessel 74, the joints 70 may be activated to move the slats 68 to the barrier configuration in which some of the slats form the composite barrier 72, as shown in FIG. 8. The composite barrier 72 is large enough to completely cover the puncture opening 76, thereby preventing blood flow through the opening. Accordingly, rather than relying on swelling of filaments as in the previous embodiments, the stent 60 repositions the slats 68 to form a fluid flow barrier.

In an alternative embodiment illustrated in FIG. 9, the sealing device may include a puncture sealing stent 80 that is positioned on an end of an introducer 82 rather than passing through the introducer during deployment. The stent 80 may include anchor and sealing sections similar to those disclosed above. In addition, the stent 80 is detachably coupled to a distal end of the introducer 82. Once the stent 80 is positioned inside the blood vessel, it may be detached from the introducer 82 and positioned appropriately with respect to the puncture opening. A tether 84 is attached to the stent 80 to assist with positioning of the stent 80. In embodiments where the stent 80 includes an EAP material, the tether 84 may also double as an electrode for carrying the activating electrical current. Alternatively, rather than being coupled to the distal end of the introducer 82, the stent 80 may be coupled to a proximal end of the introducer and subsequently slid toward the distal end during deployment.

Figure 10:
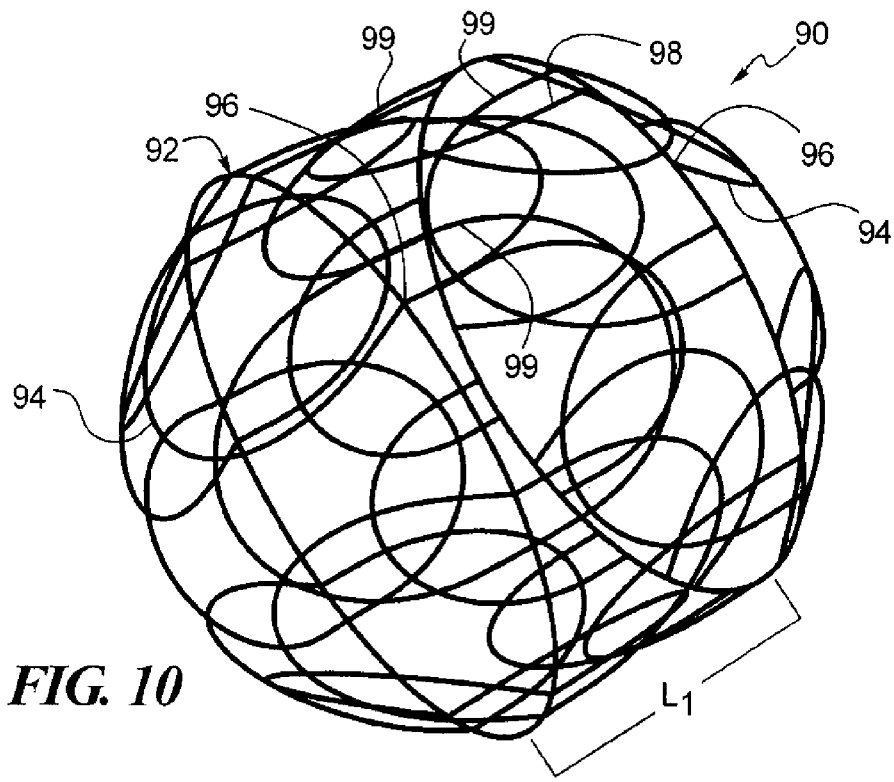
FIGS. 10 and 11 are perspective views of a stent base frame in the delivery and deployed configurations, respectively.
Figure 11:
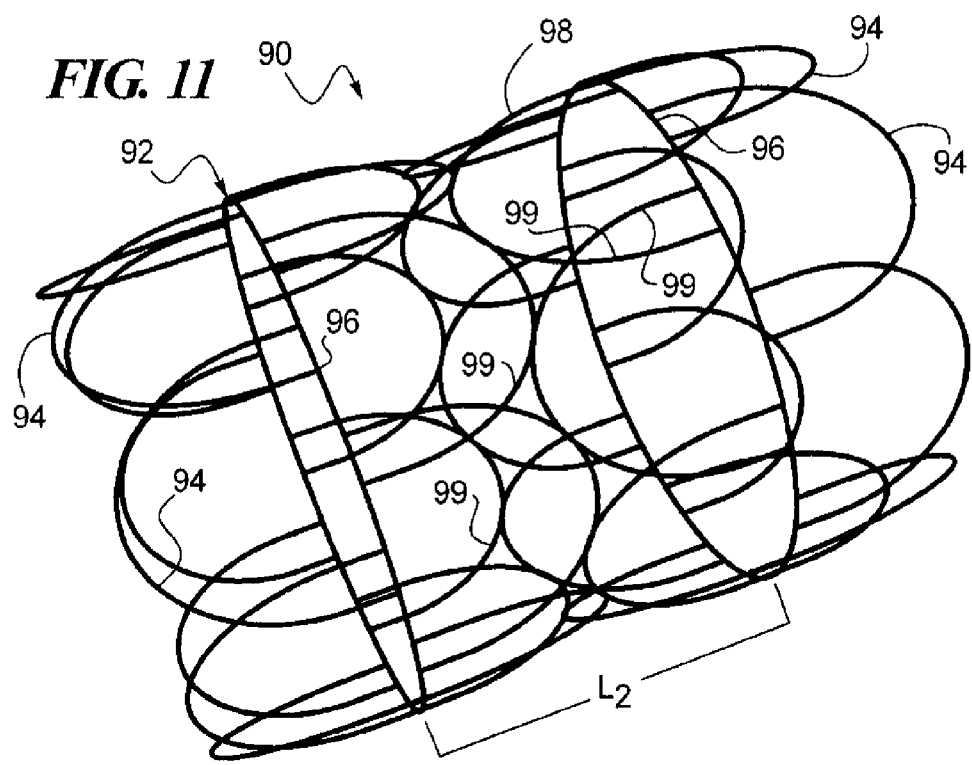
Figure 15:
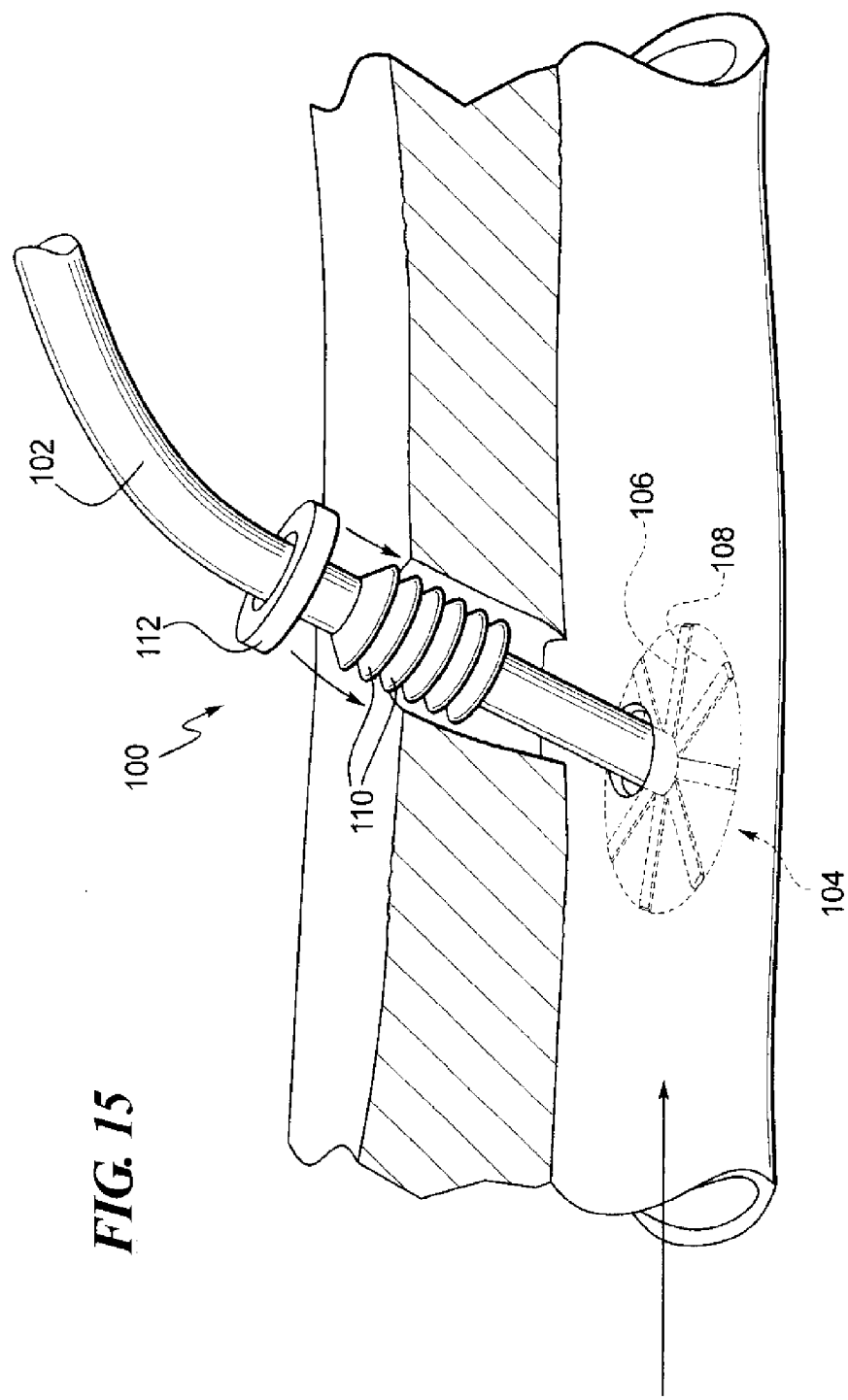
FIG. 15 is a perspective view of the sealing device of FIG. 12 during insertion into the blood vessel.

In addition to facilitating formation of a fluid barrier, the expandable material may also be used to actuate base frame between delivery and deployed configurations. As shown in FIGS. 10 and 11, a stent 90 may comprise a base frame 92 that is movable between the contracted, delivery configuration (FIG. 10) and the expanded, deployed configuration (FIG. 11). It should be noted that FIGS. 10 and 11 show a sub-frame only, and that the stent 90 may include additional components, such as filaments formed of expandable material, in accordance with the present disclosure. The sub-frame 92 includes arms 94 that are pivotably joined at hinges 96 to a main body section 98 of the frame. An expandable material, such as EAP, may be positioned between the main body section 98 and each arm 94 to actuate the arms 94, thereby driving the stent 90 from the delivery configuration to the deployed configuration. For example, with the EAP in an initial, reduced volume configuration, the arms 94 may be in a collapsed position corresponding to the contracted configuration of the stent 90. The EAP may then expand to an enlarged volume configuration that forces the arms 94 to an extended position corresponding to the expanded configuration of the stent 90.

The main body section 98 has segments 99 that may also be slidable relative to one another and therefore may also be driven by the expandable material to move between contracted and expanded configurations. In particular, and as shown in FIGS. 10 and 11, the main body section 98 has a first length "L1" in the contracted configuration and a second length "L2" in the expanded configuration. The main body section 98 may include expandable material positioned to effect the change in length.

A further alternative embodiment of a vessel sealing device is illustrated in FIGS. 12-15. This embodiment includes an umbrella-like plug 100 having initial and barrier configurations. More specifically, the plug 100 includes a stem 102 and an expandable seal 104 coupled to a distal end of the stem 102. A base frame for the plug 100 is formed by radially extending supports 106 hingedly attached to the stem 102. The supports 106 are movable from a delivery configuration, in which they overlie the stem 102, to a deployed configuration, in which they extend substantially normal to an axis of the stem 102, as illustrated in FIGS. 12 and 13, respectively. A seal membrane 108 is attached to the supports 106 and is movable from an initial configuration to a barrier configuration, in which it is sized to block the blood vessel puncture. Suitable materials for the membrane include collagen, ePTFE, and a thin biodegradable polymer (i.e., the general class of polyesters [such as polyactide, poly(E-caprolactone), polytartrates], or polyanhydrides [such as a copolymer of sebacic acid and 1,3-bis(p-carboxyphenoxy)propane or a copolymer of sebacic acid and fumaric acid]). The stem 102 also includes a series of annular pawls 110. A clamp ring 112 is provided having an inner diameter sized to form an interference fit with the pawls 110.

In operation, and with the supports 106 mechanically restricted by an introducer 116 to be held in the delivery configuration, the stem 102 and seal 104 are advanced through a lumen 114 of the introducer 116 until the seal 104 extends past the distal end of the introducer 116 and into the blood vessel. The stem 102 is then retracted proximally so that the supports 106 move to the deployed configuration, thereby unfolding the membrane 108 into the barrier configuration. The introducer 116 may then be completely withdrawn from the patient. The clamp ring 112 is then advanced over the pawls 110, which are preferably spaced from the seal 104 so that they are positioned adjacent the skin surface of the patient, to lock the seal 104 in place. Any excess portion of the stem 102 located proximally of the clamp ring 112 may be cut off. Accordingly, this embodiment not only provides a seal for the puncture opening but also may apply pressure through the use of the clamp ring 112.

In each of the embodiments described above, the entire sealing device structure may be formed of a bio-absorbable material to minimize potential interference during future interventions. Such materials will simply dissolve over time, leaving no permanent structure within the vessel.

While the foregoing was written with reference to specific examples and embodiments, it is to be understood that the scope of this disclosure is not to be limited thereby, but rather they are provided to satisfy best mode and enablement requirements while providing support for any and all claims which may issue herefrom.

What is claimed is:

1. A sealing device for percutaneously sealing a puncture opening in a wall of a blood vessel, the sealing device comprising:
   a cylindrical base frame having a sealing section coupled thereto and defining a longitudinal axis;
   wherein the base frame is movable between a delivery configuration in which the base frame is retracted to have a relatively smaller overall profile and a deployed configuration in which the base frame is extended to have a relatively larger overall profile;
   wherein the base frame is sized to engage an interior surface of the blood vessel wall when in the deployed configuration;
   wherein the sealing section is configured to prevent fluid flow through the puncture opening while permitting fluid flow through the blood vessel in the deployed configuration;

further including a tether attached at a middle portion of the sealing section;
wherein the tether extends away from the middle portion of the sealing section transversely relative to the longitudinal axis;
wherein the sealing section comprises a bi-stable sealing structure having a first stable state corresponding to an initial configuration and a second stable state corresponding to a barrier configuration;
wherein the sealing section comprises a plurality of braided sealing filaments;
wherein the sealing filaments comprise an expandable material, wherein each filament has a smaller volume in the initial configuration and a larger volume in the barrier configuration;
wherein the expandable material comprises an electroactive polymer that selectively moves from the initial configuration to the barrier configuration in response to an electric current supplied to the expandable material.

* * * * *